(12) United States Patent
Wilson

(10) Patent No.: US 9,295,635 B2
(45) Date of Patent: *Mar. 29, 2016

(54) LIP GLOSS

(71) Applicant: MARY KAY INC., Dallas, TX (US)

(72) Inventor: Kim Wilson, Aledo, TX (US)

(73) Assignee: Mary Kay Inc., Addison, TX (US)

( * ) Notice: Subject to any disclaimer, the term of this patent is extended or adjusted under 35 U.S.C. 154(b) by 112 days.

This patent is subject to a terminal disclaimer.

(21) Appl. No.: 14/303,256

(22) Filed: Jun. 12, 2014

(65) Prior Publication Data

US 2014/0363390 A1    Dec. 11, 2014

Related U.S. Application Data

(63) Continuation of application No. 13/323,349, filed on Dec. 12, 2011, now Pat. No. 8,790,030.

(60) Provisional application No. 61/422,541, filed on Dec. 13, 2010.

(51) Int. Cl.

| | |
|---|---|
| *A61K 8/96* | (2006.01) |
| *A61Q 1/04* | (2006.01) |
| *A61K 8/67* | (2006.01) |
| *A61K 8/81* | (2006.01) |
| *A61Q 19/00* | (2006.01) |
| *A61Q 19/08* | (2006.01) |
| *A61K 8/92* | (2006.01) |
| *A61K 8/97* | (2006.01) |
| *A61K 8/63* | (2006.01) |

(52) U.S. Cl.
CPC . *A61K 8/965* (2013.01); *A61K 8/63* (2013.01); *A61K 8/676* (2013.01); *A61K 8/8117* (2013.01); *A61K 8/92* (2013.01); *A61K 8/97* (2013.01); *A61Q 1/04* (2013.01); *A61Q 19/001* (2013.01); *A61Q 19/08* (2013.01); *A61K 2800/31* (2013.01); *A61K 2800/48* (2013.01)

(58) Field of Classification Search
CPC .................................................. A61Q 1/04
USPC ............................................................. 424/64
See application file for complete search history.

(56) References Cited

U.S. PATENT DOCUMENTS

| | | | |
|---|---|---|---|
| 6,800,292 B1 | 10/2004 | Murad | 424/401 |
| 2006/0002884 A1 | 1/2006 | Golz-Berner et al. | 424/74 |
| 2008/0213323 A1 | 9/2008 | De Lacharriere et al. | 424/401 |
| 2009/0169652 A1 | 7/2009 | Osborne | 424/727 |
| 2010/0247563 A1 | 9/2010 | Hines et al. | 424/195.16 |

FOREIGN PATENT DOCUMENTS

| | | |
|---|---|---|
| EP | 19992322 | 11/2008 |
| KR | 10-2010-0128137 | 12/2010 |

OTHER PUBLICATIONS

Tiens International. "Tiens Aprotie Cosmetic Lipstick Collection". Sep. 10, 2010.
PCT International Search Report and Written Opinion issued in PCT Patent Application No. PCT/US2011/064436, dated Jul. 24, 2012.

*Primary Examiner* — Jake Vu
(74) *Attorney, Agent, or Firm* — Norton Rose Fulbright US LLP

(57) ABSTRACT

Disclosed are compositions and methods for their use that include pomegranate extract having pomegranate sterols and shale extract having water-soluble minerals.

14 Claims, No Drawings

LIP GLOSS

CROSS REFERENCE TO RELATED APPLICATIONS

This application is a continuation of U.S. application Ser. No. 13/323,349 filed Dec. 12, 2011, which claims the benefit of U.S. Provisional Application No. 61/422,541, filed Dec. 13, 2010. The contents of the referenced applications are incorporated herein by reference.

BACKGROUND OF THE INVENTION

A. Field of the Invention

The present invention relates generally to compositions that can be used to improve the skin's visual appearance. In one particular aspect, the compositions concern formulations that can be used to treat skin in and around the lips (e.g., lipsticks, lip glosses, lip balms, etc.). The compositions of the present invention can have an enhanced shine or color when compared with such formulations currently on the market.

B. Description of Related Art

Previous attempts at lip-based products such as lip glosses have either lacked substantivity, tended to pool on the skin, or lacked the ability to effectively treat or prevent lip-related conditions (e.g., dried or cracked lips, lip wrinkles, etc.). Attempts to solve the substantivity and pooling problems resulted in highly viscous formulations that were difficult to spread on the lips, had unpleasant tactile properties (e.g., heavy, oily, tacky, etc.), and tended to clump or cake together. This resulted in lips that had an unpleasant aesthetic appearance and a streaky/non-uniform coloring.

Attempts to solve the lip treatment problems resulted in unstable formulations or formulations that simply failed to provide the user with an effective amount of the active. The instability oftentimes was attributed to the active ingredients in that such ingredients adversely affected the viscosity of the formulation. A lip gloss that was too thin tended to pool, which resulted in uneven lip protection, as the actives also pooled together. A lip gloss that was too thick caked or clumped together, which resulted in uneven application of the product on the lips. A lip gloss that had the right viscosity had limited amounts of the active, which resulted in a product that failed to effectively treat lip-related conditions.

SUMMARY OF THE INVENTION

The inventor found a solution to the aforementioned problems. This solution results in a lip gloss formulation that is substantive, does not pool on the lips, is easy to spread, and has effective amounts of actives to moisturize the lips, treat dry, chapped, or cracked lips, and reduce or prevent the appearance of lip wrinkles. The lip gloss also has pleasant tactile properties and provides aesthetically pleasing visual appearance on the lips.

The inventor also discovered that a unique combination of shale extract and pomegranate extract having pomegranate sterols provides a synergistic effect in treating lips. The synergism is derived from the pomegranate extract's ability to bind to and hold water on the surface of the skin and the shale extract's ability to use such water as a way to enhance skin absorption of minerals within the shale extract. Both the water on the lips, which provides moisturization and hydration, and the skin's enhanced absorption of minerals within the shale extract, which provides antioxidant effects, actively treats dry, chapped, chaffed, and/or cracked, lips while also preventing the deleterious effects of oxidation. The end result includes moist and hydrated lips and reduced appearance of lip wrinkles.

The synergistic combination of shale extract and pomegranate extract having pomegranate sterols can also be extended to skin other than the lips. For instance, compositions having a combination of these ingredients can be used on facial skin (e.g., chin, cheeks, nose, periorbital region, forehead), chest skin, arm skin, hand skin, back skin, leg skin, foot skin, etc. Such compositions can be used to prevent or treat a wide range of skin conditions, many of which are disclosed throughout this specification. In one aspect, the compositions can be used to prevent or treat the appearance of skin aging (e.g., reduce or prevent the appearance of fine lines and wrinkles). Further, such compositions can be used to moisturize skin or hydrate skin, disinfect skin or skin wounds or burned skin, or treat or prevent a wide variety of skin conditions disclosed throughout this specification.

In one aspect, there is a liquid or semi-solid composition comprising a gel base comprising a hydrogenated polymer and a copolymer, a wax, pomegranate extract that includes pomegranate sterols, shale extract that includes water-soluble minerals, an oil soluble vitamin C derivative, and optionally a pigment, wherein the composition is anhydrous. A semi-solid composition is a composition that has a viscosity and rigidity intermediate between that of a solid and a liquid. Non-limiting examples of semi-solid substances include stiff dough or firm gelatin. In certain aspects, the hydrogenated polymer can be hydrogenated polyisobutene and the copolymer can be a butylene/ethtylene/styrene copolymer or an ethylene/propylene/styrene copolymer or a combination thereof. The oil soluble vitamin C derivative can be tetrahexyldecyl ascorbate. In certain aspects, the composition can be paraben free, hydroxyl acid free, carmine free, ceramide or ceramide precursor free, and/or dimethicone or cyclomethicone free. In particular instances, the wax can be ozokerite. In one embodiment, the composition includes at least 40% by weight of the gel base, 3 to 7% by weight of the wax, 0.01 to 2% by weight of the pomegranate extract, 0.01 to 2% by weight of the shale extract, 0.01 to 2% by weight of the oil soluble vitamin C derivative, and 3 to 7% by weight of a pigment or mixture of pigments. In one aspect, the inventor discovered that a weight ratio between the gel base to the wax of between 15:1 to 17:1 and/or the weight ratio of the wax to the shale extract between 30:1 to 40:1 or between 35:1 to 37.5:1 produces a viscosity that is acceptable for a lip gloss yet still retains the effectiveness of the shale extract. In certain aspects, the composition is a lip gloss. The lip gloss can be comprised in an elongated container that includes a wand or an applicator tip, wherein the tip is at least partially convex. In a particular embodiment, the lip gloss is anhydrous and includes the Table 1 ingredients and amounts of such ingredients. The Table 1 composition is incorporated into this section by reference.

Also disclosed is a mixture comprising pomegranate extract that includes pomegranate sterols and shale extract that includes water-soluble minerals. The mixture can be in powdered form or liquid form. The shale extract can be an aqueous extract and/or the pomegranate extract can be an oil extract. The mixture can consist essentially of or consists of pomegranate and shale extracts. The mixture can be included in a cosmetic, food, or drug product.

Also disclosed is a method for treating dried, cracked, or chapped lips or preventing or reducing the appearance of lip wrinkles comprising topically applying any one of the compositions disclosed in this application or any one of the mixtures disclosed in this application to dried, cracked, or chapped lips or to skin in need of prevention or reduction of lip wrinkles, wherein topical application of the compositions or mixtures treats dried, cracked, or chapped lips or prevents or reduces the appearance of lip wrinkles. The composition can be applied directly onto the lips or can be applied onto lips that already have lipstick or lip balm applied thereon.

In yet another embodiment there is disclosed a method of treating a fine line or wrinkle comprising topically applying to a fine line or wrinkle a composition comprising pomegranate extract that includes pomegranate sterols and shale extract that includes water-soluble minerals, wherein topical application of said composition to a fine line or wrinkle treats said fine line or wrinkle.

Also disclosed is a method of treating erythemic skin comprising topically applying to skin in need thereof a composition comprising pomegranate extract that includes pomegranate sterols and shale extract that includes water-soluble minerals, wherein topical application of said composition to erythemic skin treats said erythemic skin.

In a further embodiment there is disclosed a method of tightening or toning skin comprising topically applying to skin in need thereof a composition comprising pomegranate extract that includes pomegranate sterols and shale extract that includes water-soluble minerals, wherein topical application of said composition to skin tightens or tones said skin.

Also disclosed is an ingestible composition comprising pomegranate extract that includes pomegranate sterols and shale extract that includes water-soluble minerals, and an ingestibly acceptable vehicle.

An injectible solution comprising pomegranate extract that includes pomegranate sterols and shale extract that includes water-soluble minerals and an injectibly acceptable solution is also contemplated.

In one aspect there is disclosed a method of treating or preventing a disease comprising administering to a person in need thereof pomegranate extract that includes pomegranate sterols and shale extract that includes water-soluble minerals, wherein the disease is treated or prevented. The disease can be AIDS, an autoimmune disease (e.g., rheumatoid arthritis, multiple sclerosis, diabetes—insulin-dependent and non-independent, systemic lupus erythematosus, or Graves disease), a cancer (e.g., malignant, benign, metastatic, or pre-cancer), a cardiovascular disease (e.g., heart disease, or coronary artery disease, stroke—ischemic and hemorrhagic, or rheumatic heart disease), diseases of the nervous system, an infection by a pathogenic microorganism (e.g., Athlete's Foot, Chickenpox, Common cold, Diarrheal diseases, Flu, Genital herpes, Malaria, Meningitis, Pneumonia, Sinusitis, Skin diseases, Strep throat, Tuberculosis, Urinary tract infections, Vaginal infections, or Viral hepatitis), inflammation (e.g., allergy, or asthma), a prion disease (e.g., CJD, kuru, GSS, or FFI), or obesity.

In one embodiment there is disclosed a composition comprising pomegranate extract that includes pomegranate sterols and shale extract that includes water-soluble minerals. The composition can be included in a topical skin formulation, an injectible composition, an edible composition, or a neutraceutical. The composition can be in the form of an edible pill or gel cap or liquid or powder, or spray or foam or is aerosolized.

In one aspect there is disclosed a method of treating or preventing hair loss comprising administering to a patient in need thereof a composition comprising pomegranate extract that includes pomegranate sterols and shale extract that includes water-soluble minerals. The composition can be topically applied to the scalp, eyebrows, or eyelashes. The composition can be in the form of an edible pill or gel cap or liquid or powder and ingested. The composition can be in the form of an injectible solution and is injected. The composition can be in the form of an aerosolized composition or a foam and sprayed onto the scalp, eyebrows, or eyelashes.

In one aspect there is disclosed a method of treating acne, burns, or scars comprising topically applying to acne, a skin burn, or a scar, a composition comprising pomegranate extract that includes pomegranate sterols and shale extract that includes water-soluble minerals, wherein the acne, burn, or scar is treated.

Also contemplated is a method of disinfecting skin or a wound comprising topically applying to skin in need of disinfection or to a wound a composition comprising pomegranate extract that includes pomegranate sterols and shale extract that includes water-soluble minerals, wherein the skin or wound is disinfected. The wound can be a cut, scrape, abrasion, incision or a burn. The burn can be skin that has been burned by the sun or by another heat source.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

One of the unique aspects of the present invention is a lip gloss formulation that has a pleasant tactile property along with effective moisturizing and anti-oxidative capabilities. The effectiveness of the lip gloss is that it has the ability to retain moisture and increase/enhance the ability of the lips to absorb anti-oxidative minerals from an aqueous extract of shale. This achievement is done despite the fact that the lip gloss is anhydrous. Not wishing to be bound by theory, it is thought that the pomegranate sterols and shale extract work in a synergistic manner such that the pomegranate sterols have the ability to bind and collect water (e.g., from the environment such as air) on the lips which can be used to solubilize the water soluble minerals in the shale extract. It is thought that this can lead to enhanced absorption of the waters-soluble minerals into the lip skin (or any skin for that matter).

These and other aspect of the present invention are described in further detail below.

A. Shale Extract

Shale extract of the present invention is an aqueous extract of humic shale that comprises hydrophilic water-soluble minerals. Because it is an aqueous extract, the extract does not include hydrophobic minerals such as metallic minerals. The extract is produced by leaching the shale with water. The liquid is collected and then subjected to spray drying, which results in a fine powder that includes the water-soluble minerals. The fine powder can then be added to any one of the formulations of the present invention. Sources of humic shale that can be used in the extraction process are widely available in the United States and throughout the world.

In addition to the extraction process described above, shale extract of the present invention can be purchased from Essential Nutrients, Inc. (South Emery, Utah, USA—http://www.essentialnutrientsinc.com/home). Note that the shale extract referenced in the Examples section of this application was obtained from Essential Nutrients, Inc.

Data suggests that water-soluble minerals that are contained in the shale extract of the present invention have antioxidative properties as well as antibacterial properties.

B. Pomegranate Extract Having Pomegranate Sterols

*Punica granatum* (pomegranate) extract having pomegranate sterols is can be obtained from the fruit or seeds of the pomegranate plant. Such an extract can be produced by disrupting the fruit or seeds by mechanical means which results in a puree. The puree can then be processed to be substantially free of impurities or undesired solids. The puree can then be subjected to various hydrophobic-based solvents (e.g., oil solvents) to extract out the sterols within the pomegranate puree. The resulting extract can be stored as a liquid or can be dried to produce a powder.

In addition, pomegranate extract with pomegranate sterols is commercially available from Active Concepts LLC (Piscataway, N.J., USA—http://www.activeconceptsllc.com/) under the trade name ABS POMEGRANATE STEROLS. Note that the pomegranate extract referenced in the Examples section of this application is ABS POMEGRANATE STEROLS.

Data suggests that pomegranate extracts that include pomegranate sterols have the ability to form hydrogen bonds with water and thereof have the ability to hold water.

C. Vitamin C

Vitamin C and corresponding derivatives thereof can also be used with the compositions of the present invention. These ingredients can further boost the antioxidative properties of the compositions. Non-limiting examples of vitamin C derivatives include ascorbyl palmitate, magnesium ascorbyl phosphate, and sodium ascorbyl phosphate. In certain instances when the composition is anhydrous or when an oil soluble vitamin C derivative is desired, then tetrahexyldecyl ascorbate can be used, which is commercially available from Barnet Products, Corp. under the trade name BV-OSC (Englewood Cliffs, N.J., USA—http://www.barnetproducts.com/). For instance, in anhydrous lipsticks and lip glosses, such as those disclosed in the present application, tetrahexyldecyl ascorbate can be used to boost the antioxidative properties of such products. Other oil soluble vitamin C derivatives are also contemplated for use with the compositions of the present invention.

D. Pigments

Pigments can be used in the compositions of the present invention to create a wide variety of visual appearances of such compositions. In certain instances, diamond pigments are used, which can create highly transparent formulations having a better luster appearance. Such pigments can also be used to create brighter colors, cleaner colors, depth, and/or sparkle to the formulations. In certain aspects, the lip products of the present invention include such pigments.

Some of the benefits of using diamond pigments include: (1) achievement of exceptionally high levels of chromaticity, color purity, brightness, transparency and reflectivity; (2) creation of brilliant, star-like glitter effect based on their smooth surfaces and large particle size; (3) production of a true multicolor effect when two or more are blended; and/or (4) addition of great visual depth and dimensionality because their novel substrate has a high level of transparency.

Diamond variable iridescent pigments use thin, precisely controlled coatings of titanium dioxide and silicone oxide on silicate platelets to separate white light into multiple component parts and produce up to three dramatic and distinct interference colors, two by reflection and one by transmission which then appear as iridescent luminosity with exceptional eye catching appeal.

Non-limiting examples of pigments that can be used in the context of the present invention include the RONASTAR®, REFLECKS®, COVAPEARL®, and CLOISONNE® line of pigments, which are commercially available from EMD Chemicals, Inc./Rona, N.J. USA (e.g., RONASTAR® NOBLE SPARKS), BASF, New Jersey USA (e.g., REFLECKS® DIMENSIONS SPARKLING RED, CLOISONNE® SATIN BRONGE, CLOISONNE® ROUGHE FLAMBE), and Sensient Cosmetic Technologies, New Jersey USA (e.g., COVAPEARL BRIGHT 933 AS).

E. Compositions of the Present Invention

It is contemplated that the compositions of the present invention can include any of the actives or any combination thereof described throughout this specification (e.g., pomegranate extract having pomegranate sterols, shale extract, and/or vitamin C derivatives). The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

F. Vehicles

The compositions of the present invention can be incorporated into all types of vehicles. As noted, above, lip products such as lipsticks, lip balms, and/or lip glosses are possible vehicles. Lip glosses, for instance are typically applied to the lips in a liquid to soft solid form. The color of lip glosses can range from clear, translucent, to various shades of opacity, and can also have a frosted, glittered, glassy, or a metallic finish. Lip glosses are typically contained in small cylindrical containers and are applied with a rounded or sloped applicator wand (e.g., doefoot applicator) or a built-in lip brush or can be contained and squeezed from tubes and applied or spread with a finger tip.

By comparison, a lipstick is in solid form and is opaque. This provides the lips with a more intense color shade when compared with a lip gloss. Also, lipsticks are housed in a lipstick case or tube. The solid nature of the lipstick allows the user to "push-up" or "push-down" the lipstick from the case or tube to expose the desired amount of surface area of the lipstick that is to be applied to the lips.

Lip balms are in a semi-solid or solid form and are typically used to relieve chapped or dry lips via providing an occlusive layer on the lip surface to seal moisture in lips and protect the lips from external exposure. By comparison, lip glosses can take a liquid to semi-solid form and also provide the user with a cosmetic function by coloring or changing the appearance of the lips.

In other non-limiting embodiments, the vehicles of the present invention can be emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

G. Cosmetic Products and Articles of Manufacture

The composition of the present invention can also be used in many cosmetic products including, but not limited to, lip sticks, lip balms, lip glosses, sunscreen products, sunless skin tanning products, hair products, finger nail products, moisturizing creams, skin benefit creams and lotions, softeners, day lotions, gels, ointments, foundations, night creams, cleansers, toners, masks, or other known cosmetic products or applications. Additionally, the cosmetic products can be formulated as leave-on or rinse-off products. In certain aspects, the compositions of the present invention are stand-alone products.

H. Additional Ingredients

In addition to the shale extract, pomegranate extract having pomegranate sterols, vitamin C derivative, and/or pigments, compositions of the present invention can include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, althea *officinalis* extract, apricot (*prunus armeniaca*) kernel oil, arginine, arginine aspartate, arnica montana extract, aspartic acid, avocado (*persea gratissima*) oil, barrier sphingolipids, butyl alcohol, beeswax, behenyl alcohol, beta-sitosterol, birch (*betula alba*) bark extract, borage (*borago officinalis*) extract, butcherbroom (*ruscus aculeatus*) extract, butylene glycol, calendula *officinalis* extract, calendula *officinalis* oil, candelilla (*euphorbia cerifera*) wax, canola oil, caprylic/capric triglyceride, cardamon (*elettaria cardamomum*) oil, carnauba (*copernicia cerifera*) wax, carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, macadamia ternifolia nut oil, maltitol, matricaria (*chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinol palmitate, rice (*oryza sativa*) bran oil, RNA, rosemary (*rosmarinus officinalis*) oil, rose oil, safflower (*carthamus tinctorius*) oil, sage (*salvia officinalis*) oil, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

I. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

The Table 1 composition is a non-limiting guideline of a lip gloss of the present invention that has moisturization and anti-oxidative properties, both of which can be used to moisturize the lips and treat lip-related conditions such as lines and wrinkles (data not shown).

TABLE 1*

| Phase** | Ingredient | Amount (%) |
|---|---|---|
| A | PARLEAM GEL ®*** | 40-50 |
|  | Hydrogenated Polyisobutene | 15-25 |
| B | C10-30 Cholesterol/Lanosterol Esters | 5-10 |
|  | Pomegranate Extract with Pomegranate Sterols | 0.01-2 |
|  | Octyl Dodecanol | 0.01-2 |
|  | Triisostearyl Citrate | 5-10 |
| C | Ozokerite | 3-7 |
|  | *Ricinus communis* Seed Oil/*Aloe barbadensis* Leaf Extract | 0.01-2 |
| D | Shale Extract | 0.01-2 |
|  | Pigments | 3-7 |

TABLE 1*-continued

| Phase** | Ingredient | Amount (%) |
|---|---|---|
| E | *Ricinus communis* Seed Oil | 0.01-2 |
| F | Tocopheryl Acetate | 0.01-2 |
|  | Retinly Palmitate | 0.01-2 |
|  | *Glycine Soja* Oil | 0.01-2 |
|  | Tetrahexyldecyl Ascorbate | 0.01-2 |
|  | Flavoring Agent | 0.01-2 |
|  | TOTAL | 100 |

*As indicated in the amount % column of Table 1, the amount of the ingredients can vary. Also, the phase A ingredients make up the gel-base of the lip gloss.
**Composition can be prepared by mixing the phase A ingredients under heat (95-100° C.). Add phase B ingredients and continue mixing under heat until mixture is homogenous. Add phase C ingredients. Cool mixture to 75-80° C. Add phase D ingredients and continue mixing. Add phase E ingredient under continued mixing. Add phase F ingredients and cool to 63-67 C and stop mixing. Let mixture cool to room temperature (20-25° C.).
***PARLEAM GEL ® is a mixture of hydrogenated polyisobutene and butylene/styrene copolymer and ethylene/styrene copolymer, which is commercially available from Rossow Cosmetiques, Laurel New York USA.

The inventor also discovered that shale extract can negatively affect the viscosity of the lip gloss to make the gloss potentially unusable/unstable. This problem was solved by identifying a particular weight ratio of the wax (ozokerite) to the shale extract, which produced a desired viscosity for the lip gloss while still retaining the lip/skin effectiveness of the shale extract. For instance, the data suggests that if shale extract is used at 0.1% by weight in the composition, then the amount of wax (e.g., ozokerite) in the composition should be at least greater than 2.77% by weight. Stated another way, wax in amounts of less than 2.77% resulted in an unstable lip gloss. The optimum amount of wax to shale extract (when shale extract is used at 0.1%) was between 3 to 4% wax, with the best stability results occurring with 3.5 to 3.75% wax. Therefore, the optimum ratio of wax to shale extract in a gel-based lip gloss of the present invention having at least 40% by weight of the gel-base is between 30:1 to 40:1, with the best results occurring with a ratio of wax to shale extract between 35:1 to 37.5:1.

Example 2

Assays that can be Used to Test Compositions

Additional assays that can be used to determine the efficacy of any one of the compositions disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with a composition of the present invention. Repeat measurements are taken at regular intervals to determine the formula's ability to reduce redness and irritation.

Skin Moisture/Hydration Assay:

Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al. (1978):

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay:

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

ORAC Assay:

Oxygen Radical Absorption (or Absorbance) Capacity (ORAC) of the aromatic skin-active ingredients and compositions can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of the aromatic skin-active ingredients and compositions can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Matrix Metalloproteinase Enzyme Activity (MMP3; MMP9) Assay:

An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methylpentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\epsilon$=13,600 M-1 cm-1 at pH 6.0 and above 7).

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claimed is:

1. A method for treating dried, cracked, or chapped lips or preventing or reducing the appearance of lip wrinkles comprising topically applying a composition to dried, cracked, or chapped lips or to skin in need of prevention or reduction of lip wrinkles, wherein the composition comprises:
   (a) a gel base;
   (b) pomegranate extract that includes pomegranate sterols;
   (c) shale extract that includes water-soluble minerals; and
   (d) optionally a pigment.

2. The method of claim 1, wherein the composition comprises:
   (a) at least 40% by weight of the gel base;
   (b) 0.01 to 2% by weight of the pomegranate extract;
   (c) 0.01 to 2% by weight of the shale extract; and
   (d) 3 to 7% by weight of a pigment or mixture of pigments.

3. The method of claim 1, wherein the composition is a lip gloss.

4. The method of claim 3, wherein the lip gloss is comprised in an elongated container that includes a wand or an applicator tip, wherein the tip is at least partially convex.

5. The method of claim 1, wherein the composition is applied to the surface of the lips or is applied to lips that already have lipstick or lip balm applied thereon.

6. The method of claim 1, wherein the composition is a semi-solid.

7. The method of claim 1, wherein the composition is a liquid.

8. The method of claim 1, wherein the gel base comprises a hydrogenated polymer and a copolymer.

9. The method of claim 8, wherein the hydrogenated polymer is hydrogenated polyisobutene and the copolymer is a butylene/ethtylene/styrene copolymer or an ethylene/propylene/styrene copolymer or a combination thereof.

10. The method of claim 1, wherein the composition is paraben free, hydroxyl acid free, carmine free, ceramide or ceramide precursor free, and dimethicone or cyclomethicone free.

11. The method of claim 1, wherein the composition further comprises a wax.

12. The method of claim 11, wherein the weight ratio of the gel base to the wax is between 15:1 to 17:1.

13. The method of claim 11, wherein the weight ratio of the wax to the shale extract is between 30:1 to 40:1 or between 35:1 to 37.5:1.

14. The method of claim 1, wherein the composition is transparent.

* * * * *